United States Patent
Maki et al.

[11] Patent Number: 5,610,306
[45] Date of Patent: Mar. 11, 1997

[54] PROCESS FOR THE PRODUCTION OF 6,13-DIHYDROQUINACRIDONES AND APPARATUS FOR USE FOR THE PRODUCTION

[75] Inventors: Hitoshi Maki; Shigeki Kato; Shinichi Azuma; Mikio Hayashi; Masatoshi Momose, all of Tokyo, Japan

[73] Assignee: Toyo Ink Manufacturing Co., Ltd., Tokyo, Japan

[21] Appl. No.: 341,969

[22] Filed: Nov. 16, 1994

[30] Foreign Application Priority Data

Nov. 19, 1993 [JP] Japan .................. 5-290293

[51] Int. Cl.⁶ .......................... C07D 471/04; C09B 48/00
[52] U.S. Cl. ................................. 546/49; 546/56
[58] Field of Search ........................ 546/49, 56

[56] References Cited

U.S. PATENT DOCUMENTS

| | | | |
|---|---|---|---|
| 2,821,529 | 1/1958 | Struve | 546/49 |
| 2,821,530 | 1/1958 | Struve | 546/49 |
| 3,024,239 | 3/1962 | Caliezi | 546/49 |
| 3,357,477 | 12/1967 | Monty | 159/6 |
| 3,357,479 | 12/1967 | Baird et al. | 159/6 |
| 3,433,790 | 3/1969 | Adachi | 546/49 |
| 3,738,988 | 6/1973 | Jackson | 546/49 |
| 4,544,746 | 10/1985 | Holtje | 546/49 |
| 4,758,664 | 7/1988 | Spietschka et al. | 546/49 |
| 4,812,568 | 3/1989 | Herzog et al. | 546/49 |
| 4,956,464 | 9/1990 | Bender et al. | 546/57 |
| 5,093,497 | 3/1992 | Schutze et al. | 546/56 |
| 5,318,626 | 6/1994 | Maki | 546/56 |

FOREIGN PATENT DOCUMENTS

| | | |
|---|---|---|
| 0204139 | 12/1986 | European Pat. Off. . |
| 0235647 | 9/1987 | European Pat. Off. . |
| 0313965 | 5/1989 | European Pat. Off. . |
| 0362690 | 4/1990 | European Pat. Off. . |
| 1605065 | 1/1973 | France . |
| 1917705 | 11/1969 | Germany . |
| 1642912 | 5/1971 | Germany . |
| 36-13833 | of 1957 | Japan . |
| 36-11630 | 7/1961 | Japan . |
| 44-3216 | 2/1969 | Japan . |
| 45-16340 | 6/1970 | Japan . |
| 52-51400 | 4/1977 | Japan . |
| 52-43497 | 10/1977 | Japan . |
| 52-134630 | 11/1977 | Japan . |
| 53-26823 | 3/1978 | Japan . |
| 54-119532 | 9/1979 | Japan . |
| 57-40562 | 3/1982 | Japan . |
| 57-57749 | 4/1982 | Japan . |
| 497915 | 10/1970 | Switzerland . |
| 1093692 | 12/1967 | United Kingdom . |
| 1106397 | 3/1968 | United Kingdom . |
| 1224132 | 3/1971 | United Kingdom . |
| 94-10249 | 5/1994 | WIPO ............................. 546/49 |

OTHER PUBLICATIONS

Ube Industries KK, Database WPI, Week 821S, Derwent Publications Ltd., London GB AN82–29928 JP–A–57040562 Mar. 1982.

*Primary Examiner*—Donald G. Daus
*Attorney, Agent, or Firm*—Wenderoth, Lind & Ponack

[57] ABSTRACT

A process for producing highly pure 6,13-dihydroquinacridone, which is a suitable intermediate for effectively producing a quinacridone pigment, for a short period of time at high yields, the process comprising providing a cylindrical reactor, providing an atmosphere free of oxygen in the cylindrical reactor, heating the cylindrical reactor so that the temperature of at least a surface of an inner wall of a cylinder of the cylindrical reactor is in the range of from 250° to 400° C., introducing a powder of 2,5-di(arylamino)-3,6-dihydroterephthalic acid dialkyl ester or a mixture of 2,5-di(arylamino)-3,6-dihydroterephthalic acid dialkyl ester with a liquid through a feed port provided in an upper portion of the cylindrical reactor, keeping the powder or the mixture in substantial contact with the inner wall of the cylindrical reactor so that an intramolecular alcohol-elimination reaction of the 2,5-di(arylamino)-3,6-dihydroterephthalic acid dialkyl ester takes place to form 6,13-dihydroquinacridone, and taking out the 6,13-dihydroquinacridone through an outlet provided in a lower portion of the cylindrical reactor.

9 Claims, 1 Drawing Sheet

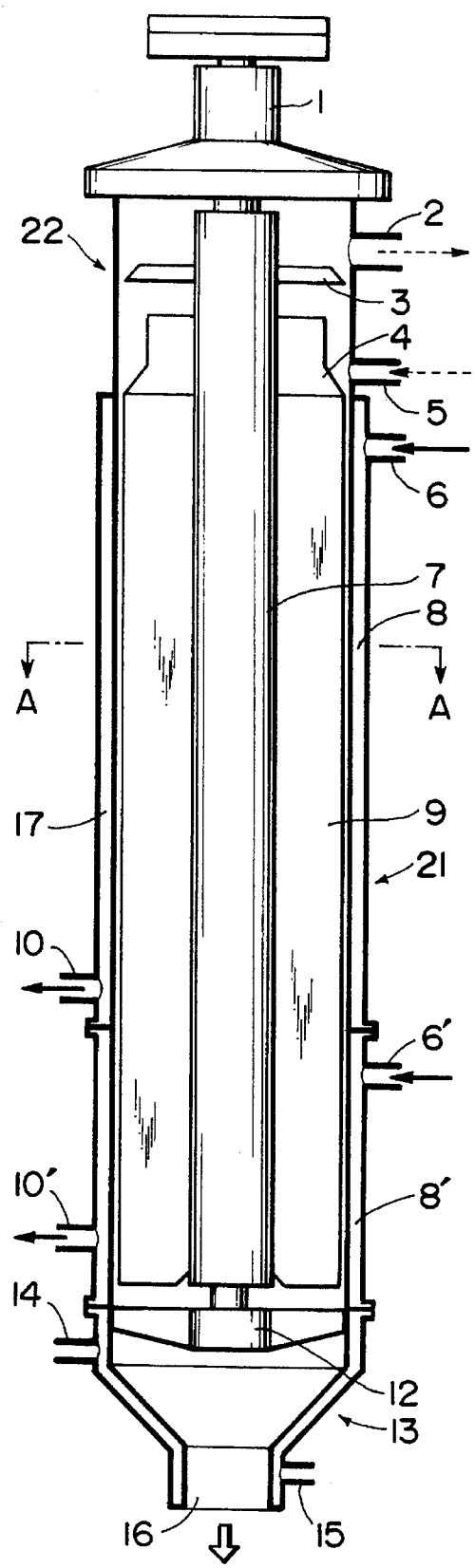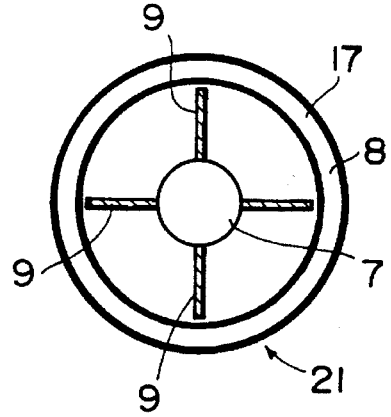

PROCESS FOR THE PRODUCTION OF 6,13-DIHYDROQUINACRIDONES AND APPARATUS FOR USE FOR THE PRODUCTION

FIELD OF THE INVENTION

The present invention relates to a process for the production of 6,13-dihydroquinacridone which is an important intermediate for the production of a quinacridone pigment, from 2,5-di(arylamino)-3,6-dihydroterephthalic acid dialkyl ester industrially advantageously with facile procedures but at a high purity and high yields; a process for the production of a quinacridone pigment; and an apparatus for use for the production of the 6,13-dihydroquinacridone.

PRIOR ART OF THE INVENTION

It is known that 6,13-dihydroquinacridone of the formula (1), which is an intermediate for the production of a quinacridone pigment,

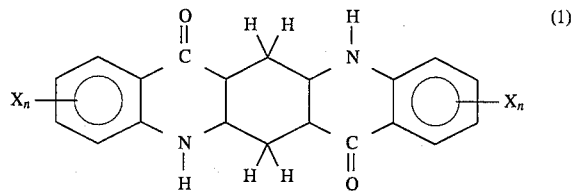

wherein X is hydrogen, F, Cl, Br, I, —OH, —$NO_2$, —$CF_3$, a $C_1$–$C_4$ alkyl group, a substituted $C_1$–$C_4$ alkyl group, a $C_1$–$C_4$ alkoxy group, a substituted $C_1$–$C_4$ alkoxy group, phenyl, cyclohexyl, phenoxy, —COOH, —COO—$C_1$–$C_4$ alkyl, –$SO_3H$, phenylamino, benzamino, —$N(CH_3)_2$, —$SO_2NH_2$, —$SO_2(CH_3)_2$, pyridino, —$CONH_2$ or —$CON(CH_3)_2$, and n is 0, 1, 3 or 4, can be produced by an intramolecular alcohol-elimination reaction of a 2,5-di(arylamino)-3,6-dihydroterephthalic acid dialkyl ester of the formula (2),

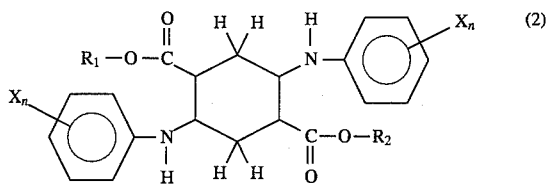

wherein each of $R_1$ and $R_2$ is a $C_1$–$C_4$ alkyl group, a substituted $C_1$–$C_4$ alkyl group, X is hydrogen, F, Cl, Br, I, —OH, —$NO_2$, —$CF_3$, a $C_1$–$C_4$ alkyl group, a substituted $C_1$–$C_4$ alkyl group, a $C_1$–$C_4$ alkoxy group, a substituted $C_1$–$C_4$ alkoxy group, phenyl, cyclohexyl, phenoxy, —COOH, —COO—$C_1$-$C_4$ alkyl, —$SO_3H$, phenylamino, benzamino, —$N(CH_3)_2$, —$SO_2NH_2$, —$SO_2(CH_3)_2$, pyridino, —$CONH_2$ or —$CON(CH_2)_2$, and n is 0, 1, 2, 3 or 4, provided that at least one ortho position relative to —NH— group has hydrogen.

The purity of the above intermediate is critical for the purity and yield of a quinacridone as an end product and the formation of a quinacridone pigment. It is known that a properly substituted quinacridone can be obtained by an oxidation of 6,13-dihydroquinacridone under predetermined conditions, while the purity of 6,13-dihydroquinacridone affects the properties of a quinacridone as an end product.

Therefore, studies have been hitherto made for improving the purity of 6,13-dihydroquinacridone, as are disclosed, for example, in Japanese Patent Publications Nos. 36-11630, 36-13833, 44-3216 and 45-16340, JP-A-52-51400, JP-B-52-43497, JP-A-52-134630, JP-A-53-26823, JP-A-54-119532, JP-A-57-40562, JP-A-57-57749, JP-A-62-205163, U.S. Pat. No. 2,821,529 and U.S. Pat. No. 2,821,530. JP-A-62-205163 corresponds to U.S. Pat. No. 4,812,568.

In methods disclosed in Japanese Patent Publications Nos. 44-3216 and 45-16340, JP-A-52-51400, JP-A-52-134630, JP-A-54-119532, JP-A-57-57749, JP-A-62-205163, U.S. Pat. No. 2,821,529 and U.S. Pat. No. 2,821,530, basically, 2,5-di(arylamino)-3,6-dihydroterephthalic acid dialkyl ester produced by a certain method is taken out of a reaction system and dissolved or dispersed in an organic solvent (described in the above publications) and the resultant solution or dispersion is heated under atmospheric pressure or elevated pressure so that an intramolecular alcohol-elimination reaction takes place to form the intended 6,13-dihydroquinacridone. However, these methods are all industrially disadvantageous since they require an additional step of separating the 6,13-dihydroquinacridone from the organic solvent.

On the other hand, JP-B-52-43497 discloses a method in which the alcohol-elimination reaction of 2,5-di(arylamino)-3,6-dihydroterephthalic acid dialkyl ester is carried out in the presence of polyphosphoric acid. Industrially advantageously, the reaction temperature is low as compared with the above methods in which the reaction is carried out in an organic solvent. Since, however, it is necessary to separate a product from the polyphosphoric acid, and since it is difficult to recover phosphoric acids, it is difficult to employ the above method in view of cost performance.

Further, JP-A-57-40562 discloses a method in which one arylamino portion of 2,5-di(arylamino)-3,6-dihydroterephthalic acid dialkyl ester is ring-closed by an alcohol-elimination reaction and the reaction product is taken out of the reaction system and then heated in a nitrogen atmosphere to cause an alcohol-elimination reaction of the other arylamino portion so that 6,13-dihydroquinacridone is produced. However, it is industrially not advantageous to carry out the reaction at two steps which can be generally carried out at one step.

According to methods disclosed in Japanese Patent Publications Nos. 36-11630 and 36-13833, 2,5-di(arylamino)-3,6-dihydroterephthalic acid dialkyl ester is subjected to a subsequent step for producing 6,13-dihydroquinacridone, without precipitating it from a synthesis solvent. In these methods, 1,4-cyclohexanedion-2,5-di(carboxylic acid ethyl ester) is synthesized from ethyl succinate in the presence, as a reaction solvent, of a mixture of biphenyl with diphenyl ether (commercially available in the trade name of "Dowtherm A"). Then, the reaction mixture is cleaned of impurities dissolved in the solvent, a large excess of an intended aromatic amino compound and a hydrochloride of the same aromatic amino compound as a catalyst are added, the resultant mixture is allowed to react under reduced pressure, and at a final point of the reaction, the reduction of pressure is terminated with nitrogen gas, followed by the neutralization of catalyst hydrochloric acid with sodium carbonate. Since the formed 2,5-di(arylamino)-3,6-dihydroterephthalic acid dialkyl ester is in a state in which it is completely dissolved in "Dowtherm A", an excess of the aromatic amino compound is distilled off under reduced pressure so that the 2,5-di(arylamino)-3,6-dihydroterephthalic acid dialkyl ester can be subjected to the subsequent step. These methods are advantageous in that the synthesis of 1,4-cyclohexanedion-2,5-di(carboxylic acid ethyl ester) from ethyl succinate and the subsequent step for producing 6,13-dihydroquinacridone are carried out in one single reactor. However, the yield of the 2,5-di(arylamino)-3,6-dihydroterephthalic acid dialkyl ester is not so high, or it is about 85%, and a large amount of energy and a long period of time are required for distilling off an excess of water and an excess of the aromatic amino compound. Further, impurities affect 6,13-dihydroquinacridone unless further filtration, washing and purification are carried out in the course of the above reactions.

JP-A-53-26823 discloses that, when 6,13-dihydroquinacridone is produced from pure 2,5-di(arylamino)-3,6-dihydroterephthalic acid dialkyl ester in the presence of "Dowtherm A", a residual aromatic amino compound greatly affects the yield and purity of the 6,13-dihydroquinacridone even if the amount of the residual aromatic amino compound dissolved is very small. It is naturally possible to separate the aromatic amino compound from "Dowtherm A" by distillation, while the complete separation of the aromatic amino compound is considered impossible in view of the solubility of the aromatic amino compound in "Dowtherm A". It is therefore not preferred to employ the method in which 6,13-dihydroquinacridone is produced from ethyl succinate through 2,5-di(arylamino)-3,6-dihydroterephthalic acid dialkyl ester in one single reactor.

Further, for overcoming the above defect, JP-A-53-26823 discloses a method in which the condensation of 1,4-cyclohexanedione-2,5-di(carboxylic acid alkyl ester) and an aromatic amino compound is carried out in the presence of an inert gas while using an excess amount of the aromatic amino compound as a reactant and a solvent, then, an inert, high-boiling point solvent such as "Dowtherm A" is poured to distill off an excess of the aromatic amino compound under reduced pressure, and a solution or slurry of the remaining 2,5-di(arylamino)-3,6-dihydroterephthalic acid dialkyl ester in the inert, high-boiling point solvent (such as "Dowtherm A") is introduced into the same inert, high-boiling point solvent which has been preheated to at least 250° C. to produce 6,13-dihydroquinacridone. However, the problem that it is required to distill off an excess of the aromatic amino compound still remains to be solved, and it is industrially not advantageous to require a long period of time and many steps for a series of procedures. Further, the 6,13-dihydroquinacridone obtained by the above method is not sufficient for producing a high-quality quinacridone by oxidation, since the above residual aromatic amino compound in a very small amount affects the quinacridone.

SUMMARY OF THE INVENTION

It is an object of the present invention to provide an industrially advantageous process for producing 6,13-dihydroquinacridone having a high purity for a short period of time at high yields.

It is another object of the present invention to provide a process for the production of 6,13-dihydroquinacridone from which quinacridone suitable as a pigment can be effectively produced.

According to the present invention, there is provided a process for the production of 6,13-dihydroquinacridone, comprising providing a cylindrical reactor, providing an atmosphere free of oxygen in the cylindrical reactor, heating the cylindrical reactor so that the temperature of at least a surface of an inner wall of a cylinder of the cylindrical reactor is in the range of from 250° to 400° C., introducing a powder of 2,5-di(arylamino)-3,6-dihydroterephthalic acid dialkyl ester or a mixture of 2,5-di(arylamino)-3,6-dihydroterephthalic acid dialkyl ester with a liquid through a feed port provided in an upper portion of the cylindrical reactor, keeping the powder or the mixture in substantial contact with the inner wall of the cylindrical reactor so that an intramolecular alcohol-elimination reaction of the 2,5-di(arylamino)-3,6-dihydroterephthalic acid dialkyl ester takes place to form 6,13-dihydroquinacridone, and taking out the 6,13-dihydroquinacridone through an outlet provided in a lower portion of the cylindrical reactor.

Further, according to the present invention, there is provided a process for the production of a quinacridone, comprising oxidizing the above-obtained 6,13-dihydroquinacridone.

Further, according to the present invention, there is provided a cylindrical reactor for the production of 6,13-dihydroquinacridone by the above process, comprising a cylinder having a hot medium inlet provided in an upper portion of the cylinder, a hot medium outlet provided in a lower portion of the cylinder and a hollow portion for circulating a hot medium, an upper cylinder extending upwardly from the cylinder, having a byproduct outlet and a feed port and having its top portion tightly closed, and a lower cone extending downwardly from the cylinder and having a product outlet, the upper cylinder being provided with a distributor for distributing a raw material fed therein, to all directions on an inner wall of the cylinder, and the cylinder being provided with an applicator for applying (spreading) and collecting the raw material repeatedly.

BRIEF DESCRIPTION OF DRAWINGS

FIG. 1 shows a cylindrical reactor used in the process for the production of 6,13-dihydroquinacridone, provided by the present invention.

FIG. 2 shows a cross section of the cylindrical reactor, taken along A—A indicated in FIG. 1.

DETAILED DESCRIPTION OF THE INVENTION

The 2,5-di(arylamino)-3,6-dihydroterephthalic acid dialkyl ester used as a raw material in the present invention has the following formula (2).

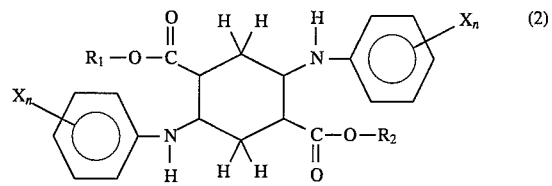

wherein each of $R_1$ and $R_2$ is a $C_1$–$C_4$ alkyl group, a substituted $C_1$–$C_4$ alkyl group, X is hydrogen, F, Cl, Br, I, —OH, —NO$_2$, —CF$_3$, a $C_1$–$C_4$ alkyl group, a substituted $C_1$–$C_4$ alkyl group, a $C_1$–$C_4$ alkoxy group, a substituted $C_1$–$C_4$ alkoxy group, phenyl, cyclohexyl, phenoxy, —COOH, —COO-$C_1$–$C_4$ alkyl, —SO$_3$H, phenylamino, benzamino, —N(CH$_3$)$_2$, —SO$_2$NH$_2$, —SO$_2$(CH$_3$)$_2$, pyridino, —CONH$_2$ or —CON(CH$_3$)$_2$, and n is 0, 1, 2, 3 or 4, provided that at least one ortho position relative to —NH— group has hydrogen.

When 6,13-dihydroquinacridone is produced from 2,5-di(arylamino)-3,6-dihydroterephthalic acid dialkyl ester, it is preferred to use 2,5-di(arylamino)-3,6-dihydroterephthalic acid dialkyl ester obtained by the condensation reaction of dialkylsuccinyl succinate and an intended aromatic amino compound of which the amount is 2.0 to 3.5 moles per mole of the dialkylsuccinyl succinate, in a solvent such as methanol, ethanol, toluene or xylene in the presence of a catalyst selected from hydrochloric acid, sulfuric acid and acetic acid in a state free of oxygen at a temperature between 60° and 130° C. for 2 to 5 hours, recovering a reaction product by filtration and washing the reaction product with the same solvent as that used for the condensation until the residual amount of aromatic amino compound is 0.1% by weight or less.

The 2,5-di(arylamino)-3,6-dihydroterephthalic acid dialkyl ester as a raw material may be fed to a ractor directly in the state of a powder, or a slurry prepared by dispersing the raw material in a liquid or a paste prepared by wetting the raw material in a liquid may be fed to a reactor. In the latter case, the amount of the liquid is 20 times as large as the amount of the raw material or less. As the liquid, an organic solvent having a boiling point of 250° to 350° C. is used. When the raw material is fed in the state of a slurry prepared by dispersing the raw material in this high-boiling-point organic solvent, the product (6,13-dihydroquinacridone) is also obtained in the state of a slurry. The high-boiling point solvent includes a eutectic mixture of diphenyl ether and biphenyl, diphenylmethane, 1,1-diphenylethane, benzyl ether, dimethyl diphenyl ether, alkylnaphthalene, a methylnaphthalene isomer mixture and a diethylnaphthalene isomer mixture. These solvents may be used alone or in combination.

As the above liquid, an organic solvent having a boiling point of lower than 250° C. is also used. When this solvent is used, the solvent is removed during the reaction step, and the product (6,13-dihydroquinacridone) is obtained as a powder. This solvent is an organic solvent inert to the conversion of 2,5-di(arylamino)-3,6-dihydroterephthalic acid dialkyl ester to 6,13-dihydroquinacridone, and is preferably selected from long-chain alkyls, alcohols, esters, glycols, ethers and aromatic compounds. More preferred are $C_1$–$C_4$ lower alkyls, $C_1$–$C_4$ lower alcohols, ethyl acetate, ethylene glycol, toluene and xylene.

FIG. 1 shows a cylindrical reactor used in the process for the production of 6,13-dihydroquinacridone, provided by the present invention. The cylindrical reactor has a cylinder 21 having a hot medium inlet 6 provided in its upper portion, a hot medium outlet 10 provided in its lower portion and a hollow portion 8 for circulating a hot medium 17, an upper cylinder 22 extending upwardly from the cylinder 21, having a byproduct outlet 2 and a feed port 5 and having its top portion tightly closed, and a lower cone 13 extending downwardly from the cylinder 21 and having a product outlet 16.

In the above embodiment of the cylindrical reactor, a hot medium is used as a means of heating the cylinder, while other heating means such as an electric heater may be used. When an electric heater is used, the hollow portion 8 provided in the cylinder is not necessary. The upper cylinder 22 has a mist separator 3 and a distributor 4. The lower cone 13 has a lower bearing lubricant inlet (not shown), a heat insulating hot medium inlet 14 and a heat insulating hot medium outlet 15.

The lower cone 13 has a bearing 12, and the upper cylinder 22 has a bearing 1. The bearings 1 and 12 support a main shaft 7, and the main shaft 7 is provided with an applicator 9.

In FIG. 1, the cylinder 21 has a two-stage structure of an upper cylinder member and a lower cylinder member, in which the lower cylinder member is also provided with a hot medium inlet 6', a hot medium outlet 10' and a hollow portion 8'.

The distributor 4 is to distribute a raw material introduced into the cylindrical reactor in all directions on the inner wall of the cylinder, and the applicator 7 is to apply and collect the raw material repeatedly.

The function of the cylindrical reactor will be explained below.

First, the cylinder is heated to a predetermined temperature, and further, the pressure in the cylinder is reduced or oxygen is discharged with an inert gas such as nitrogen or argon. Then, a powder of 2,5-di(arylamino)-3,6-dihydroterephthalic acid dialkyl ester or a mixture of 2,5-di(arylamino)-3,6-dihydroterephthalic acid dialkyl ester with a liquid is gradually introduced into the cylindrical reactor through the feed port 5. The powder or the mixture is distributed in all directions on the inner wall of the cylinder with the distributor 4. The powder or the mixture goes downward keeping substantial contact with the inner wall of the cylindrical reactor, during which an alcohol-elimination reaction proceeds. In the cylindrical reactor, the applicator 9 attached to the main shaft 7 supported with the bearings 1 and 12 applies and collects the powder or the mixture to/from the inner wall repeatedly, during which the reaction proceeds. Lower alcohols generated during the reaction are vaporized and discharged from the reaction system through a gas outlet 2. In the embodiment of the cylindrical reactor shown in FIG. 1, in which the cylinder is separated into the upper cylinder member and the lower cylinder member at a portion ⅔ of the length of the reactor far from its top, when the temperature in the lower cylinder member is set at a temperature higher than the boiling point of a solvent used, the solvent is evaporated from a slurry of a product and the solvent, and 6,13-dihydroquinacridone can be taken through the outlet 16 in the form of a dry powder. When no lower cylinder member is used, or when the temperature in the lower cylinder is set around the boiling point of the solvent, 6,13-dihydroquinacridone is taken out through the outlet 16 in the form of a paste.

The applicator 9 used in the cylindrical reactor of the present invention is not necessarily required to have a form shown in FIG. 2. It may have the form of a spiral, a screw, a hammer, a roller or a sliding blade. The rotation rate, measured on the top of the applicator, is preferably 6.0 to 10.0 m/second. The gap between the inner wall of the cylinder and the top of the applicator is 4 mm or less at the largest, and it is preferably 0.1 to 2 mm. The cylindrical reactor may be formed of any one of a metal, glass, etc. The applicator 9 is not essential in the present invention, while it is preferred to use the applicator 9 for proceeding with the reaction uniformly.

The temperature of the inner wall surface of the cylinder is set at a temperature in the range of from 250° to 400° C., preferably 250° to 350° C. The amount of 2,5-di(arylamino)-3,6-dihydroterephthalic acid dialkyl ester to be fed into the cylindrical reactor is determined in proportion to the diameter and the length (heat transfer area) of the cylinder and depending upon the content of the solvent, while the above amount of 2,5-di(arylamino)-3,6-dihydroterephthalic acid dialkyl ester is also adjusted so that lower alcohols generated together with the conversion of the above material into 6,13-dihydroquinacridone is quantitatively distilled off. When the mixture is fed by spraying, the spraying pressure is set in the wide range of from 3 to 200 kg/cm²G. Further, basically, the interior of the cylindrical reactor is required to be free of oxygen. However, when an inert gas of nitrogen or argon is used, preferably, the inert gas is introduced from a lower portion of the cylindrical reactor so that it forms a moderate gas flow at a flow rate of about 0.01 to 5 m/second upwardly to the gas outlet provided in an upper portion of the cylindrical reactor. When the interior of the cylindrical reactor is imparted with an atmosphere free of oxygen by reducing the pressure in the reactor, it is preferred to reduce the pressure to 250 mmHg or less.

When the 6,13-dihydroquinacridone produced by the process of the present invention is taken out in the form of a paste which is a mixture of the 6,13-dihydroquinacridone with the organic solvent, it is preferred to remove the organic solvent by washing the paste with a $C_1$–$C_4$ lower alcohol such as methanol, ethanol, n-propanol or iso-propanol. Quinacridone can be obtained from any one of the above 6,13-dihydroquinacridone paste containing the above lower alcohol and a product prepared by drying the above paste.

The 6,13-dihydroquinacridone produced by the process of the present invention can be converted to the corresponding quinacridone by oxidation with an oxidizing agent in a solvent in the presence of an alkali at a high temperature and optionally under elevated pressure and optionally in the presence of a dispersing agent and a reaction promoter. The oxidizing agent is selected from sodium m-nitrobenzenesulfonate, nitrobenzene, nitronaphthalene, nitrobenzenesulfonic acid, nitrobenzenecarboxylic acid, nitrophenol, sodium anthraquinonesulfonate, sodium polysulfide and air. The solvent is selected from methanol, ethanol, acetone and a mixed solvent of ethylene glycol or glycol ether with water. Preferably, the oxidation is carried out with air in the presence of a dispersing agent, preferably an anionic dispersing agent such as a condensate of aromatic sulfonic acid and formaldehyde, and the quinacridone is formed as coarse particles. These particles require a so-called pigmentation step of finely milling the particles for use them as a coloring material.

The oxidation of 6,13-dihydroquinacridone is a solid-liquid or a solid-gas layer reaction in which the 6,13-dihydroquinacridone particles form cores to be oxidized, since the 6,13-dihydroquinacridone itself is poor in solubility in organic solvents. Practically, it is therefore impossible to obtain quinacridone particles having a smaller size than the starting 6,13-dihydroquinacridone particles. In other words, the pigmentation step can be omitted only when 6,13-dihydroquinacridone having a particle size smaller than the particle size suitable for a pigment is oxidized.

However, the 6,13-dihydroquinacridone obtained by the process of the present invention can be converted to 6,13-dihydroquinacridone particles having a specific surface area of at least 20 $m^2$/g and having uniform particle diameters by forming it in a salt in a solution containing 40 to 96% by weight of a $C_1$–$C_4$ lower alcohol, 4 to 30% by weight of sodium hydroxide or potassium hydroxide and 0 to 30% by weight of water, and then adding mineral acid, water or an alcohol to hydrolyze the salt in an alkali concentration lower than a stoichiometric amount. Then, the so-prepared 6,13-dihydroquinacridone is oxidized with an oxidizing agent selected from nitrobenzenesulfonic acid, nitrobenzene, substituted nitrobenzene, anthraquinonesulfonic acid, sodium polysulfide and oxygen in a $C_1$–$C_4$ alcohol solution containing 1.5 to 20% by weight of sodium hydroxide or potassium hydroxide and 2 to 40% by weight of water, whereby there can be produced an unconventional quinacridone substituted as required, which does not require the pigmentation step.

6,13-Dihydroquinacridone easily forms a salt in an alcohol solution in the presence of an alkali. That is because a >C=O group bonds to Na or g similarly to quinacridone, and clearly, the alkali is required in an amount of at least 2 mol (at least a stoichiometric amount) per mole of 6,13-dihydroquinacridone. On the other hand, when the amount of the alkali is reduced to a level smaller than the stoichiometric amount, the salt of 6,13-dihydroquinacridone is hydrolyzed. The 6,13-dihydroquinacridone particles formed by the above hydrolysis are obtained as particles having a specific surface area of at least 20 $m^2$/g, and as a result, an excellent quinacridone pigment can be obtained.

The formation of a quinacridone pigment is most preferably carried out as follows. That is, a highly pure 6,13-dihydroquinacridone is charged into a proper reactor having a stirrer and a refluxing device together with a $C_1$–$C_4$ lower alcohol as part of a solvent and a necessary amount of a water-soluble alkali. When the mixture (system) is stirred, the 6,13-dihydroquinacridone and the alkali form a salt. The solvent is selected from methanol, ethanol, n-propanol, iso-propanol, n-butanol and iso-butanol, and methanol is preferred. The water-soluble alkali is selected from sodium hydroxide and potassium hydroxide, and sodium hydroxide is preferred in view of an ease with which the salt is formed, economic performance and an ease with which the particles can be controlled. For improving the solubility in the alkali in the system, it is preferred to add water in a small amount (preferably, in the same amount as that of the alkali). The amount of the solvent is 3 to 30 times, preferably 5 to 15 times, as large as the amount of the 6,13-dihydroquinacridone, and the solvent contains 40 to 96% by weight of the alcohol, 4 to 30% by weight of the water-soluble alkali and 0 to 30% by weight of water, preferably 70 to 88% by weight of the alcohol, 6 to 20% by weight of the water-soluble alkali and 6 to 20% by weight of water. The formation of a salt proceeds at a relatively high rate, while it easily proceeds when the alkali concentration is high. When the 6,13-dihydroquinacridone is formed into a salt, the salt is formed as a large crystal having a size of about 30 μm. When a mineral acid such as sulfuric acid or hydrochloric acid, water or an alcohol is added to the salt, the salt is hydrolyzed to give fine 6,13-dihydroquinacridone particles having a specific surface area of 20 to 40 $m^2$/g.

After the initiation of the oxidation, the solvent composition of the solution containing the above 6,13-dihydroquinacridone is converted to an alcohol solution containing 1.5 to 20% by weight of water-soluble alkali and 2 to 30% by weight of water. When the alkali concentration of the system is less than the salt-forming concentration, the oxidation can be initiated without adjusting the concentration without any problem. However, when the system has an alkali concentration higher than the salt-forming concentration, 6,13-dihydroquinacridone again forms a salt. Therefore, the pure, intended quinacridone substituted as required can be obtained only when the alkali concentration is adjusted after the initiation of the oxidation. The oxidizing agent is selected from nitrobenzenesulfonic acids, nitrobenzene, substituted nitrobenzene, anthraquinonesulfonic acid, sodium polysulfide and oxygen. Above all, sodium m-nitrobenzenesulfonate is preferred since the oxidation proceeds moderately. With a strong oxidizing agent such as oxygen, the oxidation is liable to proceed easily to form quinacridonequinone. When the alkali concentration is adjusted to 1.5 to 20% by weight when the oxidation is carried out, quinacridone can be obtained as uniform particles having a specific surface area of 10 to 40 $m^2$/g.

Further, when the 6,13-dihydroquinacridone is oxidized, 1 to 20% by weight of a quinacridone pigment derivative such as a basic quinacridone pigment derivative disclosed in EP-B-362690 (which corresponds to U.S. Pat. No. 5,368, 641) or an acidic or neutral quinacridone pigment derivative of the formula (3) may be added so that the quinacridone pigment may be controlled to have a preferred crystal state or may have advantageous surface properties and practically advantageous properties.

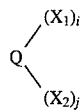

wherein Q is a quinacridone residue, which is not substituted or substituted with a halogen atom, a $C_1$–$C_4$ alkyl group, a $C_1$–$C_4$ alkoxy group, $H_2$—CO— or a $C_1$–$C_4$ alkyl-NH—CO— group, each of $X_1$ and $X_2$ is different from the other and is a hydrogen atom, a halogen atom (when one of $X_1$ and $X_2$ is a hydrogen atom and the other is a halogen atom, the number of the halogen atoms is at least 2) or any one of substituents of the formula (4), and each of i and j is independently an integer of 1 to 4.

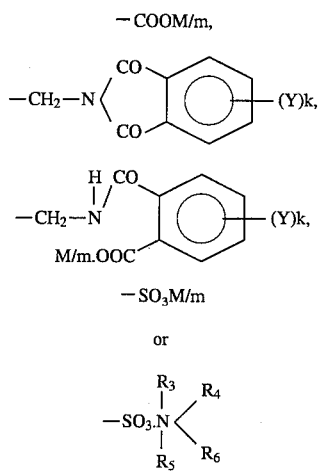

wherein Y is a hydrogen atom, a halogen atom, —$NO_2$, —$NH_2$ or —$SO_3H$, M is a hydrogen atom, a calcium atom, a barium atom, a strontium atom or an aluminum atom, each of $R_3$, $R_4$, $R_5$ and $R_6$ is a hydrogen atom (excluding the case where all of $R_3$, $R_4$, $R_5$ and $R_6$ are hydrogen atoms) or an alkyl group having 1 to 30 carbon atoms, k is an integer of 1 to 4, and m is a valence of M.

Further, when the 6,13-dihydroquinacridone is oxidized, a quinacridone which has a desired crystal form and is substituted as required is added as described in JP-B-56-45434, whereby there can be obtained a quinacridone which has a desired crystal form and is substituted as required.

From the 6,13-dihydroquinacridone obtained according to the present invention, the following quinacridones can be synthesized. Quinacridone, 2,9-dichloroquinacridone, 3,10-dichloroquinacridone, 4,11-dichloroquinacridone, 2,3,9,10-tetrachloroquinacridone, 2,4,9,11-tetrachloroquinacridone, 2,9-difluoroquinacridone, 2,9-dibromoquinacridone, 2,9-dimethylquinacridone, 3,10-dimethylquinacridone, 4,11-dimethylquinacridone, 2,4,9,11-tetramethylquinacridone, 2,9-di(tert-butyl)quinacridone, 2,9-dihydroxylquinacridone, 2,9-di(trifluoromethyl)quinacridone, 2,9-dimethoxyquinacridone, 2,9-diethoxyquinacridone, 2,4,9,11-tetramethoxyquinacridone, 2,9-dicarboxyquinacridone, 2,9-dicyclohexylquinacridone, 2,9-diphenylquinacridone, 2,9-di(dimethylamino)quinacridone, 2,9-di(dimethylaminosulfo)quinacridone, 2,9-di(dimethylaminocarbonyl)quinacridone, 3,10-dinitroquinacridone, 2,9-dimethyl-4,11-dichloroquinacridone, 2,9-dimethyl-4,11-dicarboxylquinacridone, and 2,9-dipyridinoquinacridone.

The quinacridone obtained from the 6,13-dihydroquinacridone produced according to the present invention is excellent in weatherability and hiding power, and can be used in a paste, a flash color, a printing colorant, an aqueous coating composition, a lacquer, a peroxide-curable varnish and a polyurethane varnish. The quinacridone obtained from the 6,13-dihydroquinacridone produced according to the present invention can be incorporated into synthetic and natural polymers including thermoplastic resins such as polyvinyl chloride, polystyrene, polyethylene, polyester, phenol plast, amino plast and rubber. Further, the quinacridone obtained from the 6,13-dihydroquinacridone produced according to the present invention can be incorporated into natural, reclaimed and synthetic fibrous materials and organic and inorganic pigments.

The quinacridone obtained from the 6,13-dihydroquinacridone produced according to the present invention can be used as a mixture in the form of a solid, an elastomer, a paste or a viscous material. For example, the aqueous paste can be prepared by adding a wetting agent or a dispersing agent to the pigment and stirring the mixture in water, or by stirring the pigment in, or kneading the pigment with, a dispersing agent in the presence of water and optionally an organic solvent or an oil. The so-obtained paste can be used, for example, for producing a flash color, a printing colorant, an aqueous coating composition, a plastic dispersion product and a spinning solution. The quinacridone obtained from the 6,13-dihydroquinacridone produced according to the present invention can be incorporated into water, an organic solvent, a non-drying oil, a drying oil, a lacquer, a varnish, a plastic and a rubber by stirring, roll-dispersing, kneading or milling the quinacridone.

EXAMPLES

The present invention will be detailed hereinafter with reference to Examples, in which "part" stands for "part by weight", and "%" stands for "% by weight".

Example 1

300 Parts of dry 2,5-dianilino-3,6-dihydroterephthalic acid dimethyl ester was dispersed in 2,000 parts of a dimethylnaphthalene isomer mixture, and the dispersion was used as a raw material for a reaction in the same cylindrical reactor as that shown in FIG. 1 under the following conditions.

| | |
|---|---|
| Raw material feeding pressure | 4 kg/cm$^2$ |
| Temperature in upper cylinder member | 280° C. |
| Temperature in lower cylinder member | 320° C. |
| Oxygen-free conditions: nitrogen gas | 0.5 m/sec. |
| Rotation rate of applicator: peripheral speed | 8.5 m/sec. |

As a result, 237 parts (95.1% of a theoretical yield) of 6,13-dihydroquinacridone was obtained. The 6,13-dihydroquinacridone had a purity of more than 99% when measured by absorbance.

Example 2

A paste (solid content at least 85%) of 300 parts of 2,5-dianilino-3,6-dihydroterephthalic acid dimethyl ester and methanol used for the synthesis thereof was used as a raw material for a reaction in the same cylindrical reactor as that shown in FIG. 1 under the following conditions.

| | |
|---|---|
| Temperature in upper cylinder member | 280° C. |
| Temperature in lower cylinder member | 290° C. |

| Oxygen-free conditions: nitrogen gas | 0.5 m/sec. |
| Rotation rate of applicator: peripheral speed | 8.5 m/sec. |

As a result, 230 parts (92.3% of a theoretical yield) of 6,13-dihydroquinacridone was obtained. The 6,13-dihydroquinacridone had a purity of more than 99% when measured by absorbance.

Example 3

300 Parts of dry 2,5-dianilino-3,6-dihydroterephthalic acid dimethyl ester was dispersed in 2,000 parts of a dimethylnaphthalene isomer mixture, and the dispersion was used as a raw material for a reaction in the same cylindrical reactor as that shown in FIG. 1 under the following conditions.

| Raw material feeding pressure | 4 kg/cm$^2$ |
| Temperature in upper cylinder member | 280° C. |
| Temperature in lower cylinder member | 280° C. |
| Oxygen-free conditions: pressure reduction | 130 mmHg |
| Rotation rate of applicator: peripheral speed | 8.5 m/sec. |

As a result, 234 parts (93.9% of a theoretical yield) of 6,13-dihydroquinacridone was obtained. The 6,13-dihydroquinacridone had a purity of more than 99% when measured by absorbance.

Example 4

300 Parts of dry 2,5-dianilino-3,6 -dihydroterephthalic acid dimethyl ester was dispersed in 2,000 parts of a dimethylnaphthalene isomer mixture, and the dispersion was used as a raw material for a reaction in the same cylindrical reactor as that shown in FIG. 1 except that the application in its central portion was omitted, under the following conditions.

| Raw material feeding pressure | 4 kg/cm$^2$ |
| Temperature in upper cylinder member | 280° C. |
| Temperature in lower cylinder member | 280° C. |
| Oxygen-free conditions: nitrogen gas | 0.5 m/sec. |

As a result, 235 parts (94.3% of a theoretical yield) of 6,13-dihydroquinacridone was obtained. The 6,13-dihydroquinacridone had a purity of more than 99% when measured by absorbance.

Example 5

The reaction in Example 1 was carried out in the same manner as in Example 1 except that 300 parts of 2,5-dianilino-3,6-dihydroterephthalic acid dimethyl ester was replaced with 300 parts of 2,5-di(p-toluidino)-3,6-dihydroterephthalic acid dimethyl ester. As a result, 239 parts (94.6% of a theoretical yield) of 2,9-dimethyl-6,13-dihydroquinacridone was obtained. The 2,9-dimethyl-6,13-dihydroquinacridone had a purity of more than 99% when measured by absorbance.

Example 6

The reaction in Example 1 was carried out in the same manner as in Example 1 except that 300 parts of 2,5-dianilino-3,6-dihydroterephthalic acid dimethyl ester was replaced with 300 parts of 2,5-di(m-chloroanilino)-3,6-dihydroterephthalic acid dimethyl ester. As a result, 240 parts (93.4% of a theoretical yield) of 3,10-dichloro-6,13-dihydroquinacridone was obtained. The 3,10-dichloro-6,13-dihydroquinacridone had a purity of more than 99% when measured by absorbance.

Example 7

The reaction in Example 1 was carried out in the same manner as in Example 1 except that 300 parts of 2,5-dianilino-3,6-dihydroterephthalic acid dimethyl ester was replaced with 300 parts of 2,5-di(2,4-dichloroanilino)-3,6-dihydroterephthalic acid dimethyl ester. As a result, 238 parts (90.6% of a theoretical yield) of 2,4,9,11-tetrachloro-6,13-dihydroquinacridone was obtained. The 2,4,9,11-tetrachloro-6,13-dihydroquinacridone had a purity of more than 99% when measured by absorbance.

Example 8

The reaction in Example 1 was carried out in the same manner as in Example 1 except that 300 parts of 2,5-dianilino-3,6-dihydroterephthalic acid dimethyl ester was replaced with 300 parts of 2,5-di(2-chloro-4-methylanilino)-3,6-dihydroterephthalic acid dimethyl ester. As a result, 236 parts (90.9% of a theoretical yield) of 4,11-dichloro-2,9-dimethyl-6,13-dihydroquinacridone was obtained. The 3,10-dichloro-6,13-dihydroquinacridone had a purity of more than 99% when measured by absorbance.

Example 9

79 Parts of methanol and 12 parts of a 50% NaOH aqueous solution were fully stirred in a stainless steel flask having a refluxing device. 10 Parts of the 6,13-dihydroquinacridone obtained in Example 1 and 10 parts of sodium m-nitrobenzenesulfonate were gradually mixed with the above-prepared solution, and the mixture was refluxed at 70° to 75° C. for 3 to 5 hours. The reaction mixture was cooled to 40° C. and filtered, and the resultant cake was cleaned with hot water until a wash liquid became colorless and transparent, to give 9.77 parts (98.3% of a theoretical value) of a nonsubstituted quinacridone. The so-obtained quinacridone was measured by IR and absorbance to show 99.2% of quinacridone and 0.8% of 6,13-dihydroquinacridone. The quinacridone had a specific surface area of 22.1 m$^2$/g.

Example 10

A stainless steel flask having a refluxing device was charged with 10 parts of the 6,13-dihydroquinacridone obtained in Example 1 and 80 parts of methanol, and the mixture was stirred. 12 Parts of a 50% NaOH aqueous solution was added, and the mixture was stirred at 40° C. for 30 minutes to form a salt. 26 Parts of 10% sulfuric acid was added to hydrolyze the salt, and the resultant solution was refluxed for 1 hour. Then, 10 parts of sodium m-nitrobenzenesulfonate was added, and immediately thereafter, 3 parts of a 50% NaOH aqueous solution was added. Then, the mixture was refluxed for 4 hours to give 9.8 parts (98.8% of a theoretical value) of a nonsubstituted quinacridone as a pigment having a uniform particle diameter. The so-obtained quinacridone had a specific surface area of 25.1 m$^2$/g.

Example 11

The experiment in Example 9 was carried out in the same manner as in Example 9 except that 10 parts of the 6,13-dihydroquinacridone was replaced with 10 parts of the 2,9-dimethyl-6,13-dihydroquinacridone obtained in Example 5, to give 9.8 parts (98.6% of a theoretical value) of 2,9-dimethylquinacridone.

Example 12

The experiment in Example 9 was carried out in the same manner as in Example 9 except that 10 parts of the 6,13-dihydroquinacridone was replaced with 10 parts of the 3,10-dichloro-6,13-dihydroquinacridone obtained in Example 6, to give 9.7 parts (97.5% of a theoretical value) of 3,10-dichloroquinacridone.

When the process for the production of 6,13-dihydroquinacridone, provided by the present invention, is carried out, 2,5-di(arylamino)-3,6-dihydroterephthalic acid dialkyl ester as a raw material may be in any one of a dry state, a wet state containing a washing solvent and a state of a mixture thereof with an inert, high-boiling point solvent conventionally used for the production of 6,13-dihydroquinacridone. The reason therefor is that the following can be reliably and industrially advantageously achieved: The reaction in which 2,5-di(arylamino)-3,6-dihydroterephthalic acid dialkyl ester is converted to 6,13-dihydroquinacridone is an endothermic reaction, 2,5-di(arylamino)-3,6-dihydroterephthalic acid dialkyl ester has a melting point lower than the temperature required for the reaction, and 2,5-di(arylamino)-3,6-dihydroterephthalic acid dialkyl ester is effectively converted to 6,13-dihydroquinacridone by heating it in an oxygen-free state.

Further, in the process for the production of 6,13-dihydroquinacridone, provided by the present invention, 6,13-dihydroquinacridone formed by setting two-stage temperatures can be taken out in any one of a dry powder state and a state of a mixture thereof with an inert, high-boiling-point solvent. These can be accomplished since 6,13-dihydroquinacridone is very stable to heat and since the present invention has fully taken into consideration the boiling point and evaporation rate of the high-boiling-point solvent.

The 6,13-dihydroquinacridone obtained by the process of the present invention has a high purity so that a quinacridone having a high purity can be also obtained at high yields at a step following the production of the 6,13-dihydroquinacridone. Particles of quinacridone obtained by a conventional method are coarse or very fine aggregates so that a pigmentation step is required, while the production of a quinacridone pigment from the 6,13-dihydroquinacridone produced by the process of the present invention easily permits crystal transition and particle control by a series of steps.

The process of the present invention obviates the use of a large amount of a solvent to which 2,5-di(arylamino)-3,6-dihydroterephthalic acid dialkyl ester is added, so that no large-sized reactor is required. Further, when 6,13-dihydroquinacridone is taken out in a dry powder state, the conventionally required step of filtration and purification is not necessary, so that the process can be simplified. Moreover, since the amount of a solvent can be decreased, the amount of energy required for the recovery of the solvent can be decreased, so that the production cost can be decreased.

What is claimed is:

1. A process for the production of a quinacridone pigment, comprising:

providing a vertical cylindrical reactor having a blade that rotates about a vertical axis of the cylindrical reactor, and providing an atmosphere free of oxygen in the cylindrical reactor;

heating the cylindrical reactor so that the temperature of at least a surface of an inner wall of a cylinder of the cylindrical reactor is in the range of from 250° to 400° C.;

introducing (i) a powder of 2,5-di(phenylamino)-3,6-dihydroterephthalic acid di-$C_{1-4}$-alkyl ester, or (ii) a mixture in the form of a slurry or paste of 2,5-di(phenylamino)-3,6-dihydroterephthalic acid di-$C_{1-4}$-alkyl ester and a liquid through a feed port provided in an upper portion of the cylindrical reactor, keeping the powder (i) or the mixture (ii) in substantial contact with the inner wall of the cylindrical reactor so that an intramolecular alcohol-elimination reaction of the 2,5-di(phenylamino)-3,6-dihydroterephthalic acid di-$C_{1-4}$-alkyl ester takes place to form 6,13-dihydroquinacridone;

taking out the 6,13-dihydroquinacridone through an outlet provided in a lower portion of the cylindrical reactor;

forming a salt of the 6-13-dihydroquinacridone in an alkali solution containing an alkali in an amount of at least 2 mol per mole of the 6,13-dihydroquinacridone, hydrolyzing the salt by reducing the alkali to an amount of less than 2 mol per mole of the 6,13-dihydroquinacridone, to obtain 6-13-dihydroquinacridone particles having a specific surface area of at least 20 $m^2/g$, and oxidizing the 6-13-dihydroquinacridone particles.

2. A process according to claim 1, wherein the mixture (ii) of 2,5-di(phenylamino)-3,6-dihydroterephthalic acid di-$C_{1-4}$-alkyl ester and a liquid is introduced and the liquid is present in an amount 20 times as large as or less than an amount of the ester.

3. A process according to claim 1, wherein the liquid is an organic solvent having a boiling point of 250° to 350° C.

4. A process according to claim 1, wherein the liquid is an organic solvent having a boiling point of lower than 250° C.

5. A process according to claim 1, wherein the liquid is inert to the formation of 6,13-dihydroquinacridone from the 2,5-di(phenylamino)-3,6-dihydroterephthalic acid di-$C_{1-4}$-alkyl ester.

6. A process according to claim 1, wherein the atmosphere free of oxygen is provided by discharging oxygen from the cylindrical reactor with an inert gas.

7. A process according to claim 1, wherein the atmosphere free of oxygen is provided by reducing a pressure in the cylindrical reactor to 250 mmHg or less.

8. A process according to claim 1, wherein the 6,13-dihydroquinacridone is oxidized in an alcohol solution containing an alkali in the presence of an oxidizing agent.

9. A process according to claim 8, wherein the alcohol solution contains 1.5 to 20% by weight of an alkali.

* * * * *